United States Patent [19]

Neal, Jr. et al.

[11] Patent Number: 4,474,755

[45] Date of Patent: Oct. 2, 1984

[54] BAGWORM MOTH ATTRACTANT AND PLANT PROTECTANT

[75] Inventors: John W. Neal, Jr., Laurel; Jerome A. Klun, Potomac; Meyer Schwarz, Kensington; Barbara A. Leonhardt, Potomac, all of Md.

[73] Assignee: The United States of America as represented by the Secretary of Agriculture, Washington, D.C.

[21] Appl. No.: 445,112

[22] Filed: Nov. 29, 1982

[51] Int. Cl.$^3$ ............................................. A01N 25/00
[52] U.S. Cl. ...................................................... 424/84
[58] Field of Search ........................................ 424/84

[56] References Cited
PUBLICATIONS

Research News, U.S. Dept. of Agriculture, Agricultural Research Service, Northeastern Region, Nov., 1981.

Notes from talk presented at Entomological Society of America by B. A. Bierl–Leonhardt in San Diego, Calif., Dec. 1, 1981.

Schlenk. Chemical Abstracts 139146p.

Primary Examiner—Stanley J. Friedman
Assistant Examiner—John M. Kilcoyne
Attorney, Agent, or Firm—M. Howard Silverstein; William E. Scott; David G. McConnell

[57] ABSTRACT

The racemate of 1-methylbutyldecanoate is synthesized and found to be a powerful attractant under field conditions for male bagworm moths. It is also found to suppress or inhibit completely the mating of female bagworm moths when applied to trees and shrubs in an effective mating suppressant or inhibiting amount.

7 Claims, No Drawings

BAGWORM MOTH ATTRACTANT AND PLANT PROTECTANT

BACKGROUND OF THE INVENTION

1. Field of the Invention

This invention relates to a novel, highly effective attractant and mating control agent for the bagworm moth, *Thyridopteryx ephemeraeformis* (Haworth), and more particularly to synthetic 1-methylbutyldecanoate and its use as an attractant, a mating control agent and plant protectant.

2. Description of the Art

Attractants for a number of species of insects, such as those for the pink bollworm moth and for the yellow jacket, are known and some of them have been used to determine the period of mating behavior by trapping the male insects. They have also been used to disrupt the mating pattern of insects and suppress, but not control completely, the insect population.

SUMMARY OF THE INVENTION

An object of this invention is to provide a synthetic attractant for the adult male bagworm moth.

Another object is to provide a mating control agent for the bagworm moth.

Still another object is to provide a method of protecting plants from being damaged by bagworm moths.

A further object is to provide a method of suppressing the number of female bagworm moths that are mated.

A still further object is to provide a method of inhibiting completely the mating of all female bagworm moths in a selected area.

In general, the above objects are accomplished by the sex attractant, synthetic racemate 1-methylbutyldecanoate and its use as an attractant for male bagworm moths. The objects are further accomplished by applying the synthetic racemate, 1-methylbutyldecanoate, to trees and shrubs in a selected area in amounts effective to suppress or inhibit completely the mating of female bagworm moths in the treated area.

DESCRIPTION OF THE INVENTION

Landscape ornamental shrubs and trees increase greatly in value as they mature and complement the area of placement. Therefore, it is important to protect them from insects that defoliate or otherwise damage the trees and shrubs. The bagworm moth is the single most important defoliator of ornamental conifers such as juniper, arborvitae, spruce and Eastern white pine in the eastern half of the United States. Although chemical pesticides can be effective, their use is objected to in many urban residential areas and in landscaped shopping centers.

Females of most lepidopteran species attract conspecific males for reproduction by emitting a sex attractant pheromone. If the active component(s) of the pheromone is isolated and identified, the compound(s) can be used as a lure in a trap to attract and catch the male of the species. However, a very real and serious deterrent to the use of a natural pheromone is the difficulty in isolating the active material and the extremely limited amount of material that is obtained.

We isolated and identified the single compound in the female bagworm moth sex pheromone as 1-methylbutyldecanoate and determined that the R enantiomer was active while the S enantiomer was inactive as a sex attractant. We also discovered that S enantiomer does not inhibit or interfere with the attractant or the plant protectant functions of the R enantiomer. This is unusual because with known insect pheromones the antipode to the active enantiomer is inhibitory to the functions of the active enantiomer. This discovery is important because it allows the use of the synthetic racemate and eliminates the need to synthesize only the R enantiomer.

Pupae were hand collected from infested conifers in the vicinity of Beltsville, Md. and were separated to sex. The females were isolated individually in 60×15 mm petri dishes and incubated at 25°–26° C. to wait emergence. Adult females, when ready for mating, rupture the anterior end of the pupal case and extend only the head and thorax. At this time the female actively sheds deciduous setae or hairs to the bottom of the bag in which they are housed. Hairs expelled by the females were aspirated onto a plug of glasswool in a pipette and washed with 50 ml hexane. The extract was concentrated and injected onto a gas chromatographic (GC) column packed with 4% SE-30 on 80/100 mesh silica. The major constituent in the extract was trapped and found to be biologically active and was purified by gas chromatography.

Capillary GC was carried out using polar and apolar 60 meter×0.25 mm (ID) fused silica columns. Low-resolution GC-MS (mass spectroscopy) showed a molecular ion at m/e 242 ($C_{15}H_{30}O_2$) and intense ions at m/e 173 and 155; high-resolution MS established that these ions were $C_{10}H_{21}O_2$ and $C_{10}H_{19}O$, respectively. No reaction occurred on treatment with $O_3$, $NaBH_4$, or acetic anhydride/pyridine; thus olefin, aldehyde, ketone or alcohol functionalities for the compound were excluded. The infrared spectrum showed absorption at 1745 cm$^{-1}$, compatible with C=O absorption of an ester. Reduction of a few µg of the compound at 250° C. with Pt and $LiAlH_4$ [B. A. Bierl-Leonhardt and E. D. deVilbiss, Anal. Chem. 53, 936, 1981] yielded n-pentane, according to GC-MS. Without Pt, a similar reduction at 300° C. gave n-decane and n-pentane. The nuclear magnetic resonance spectrum of the compound showed a triplet at 2.3 ppm ($CH_2C=O$) and multiplet at 4.9 ppm (CHO).

The natural ester (ca. 1 µg) was reduced with $LiAlH_4$ in $CCl_4$ and the resulting 2-pentanol was derivatized with Mosher's reagent [J. A. Dale, D. L. Dull and H. S. Mosher, J. Org. Chem. 34, 2543, 1969]. The GC retention time of this diastereomeric derivative was identical to that of the Mosher's derivative of authentic (R)-2-pentanol.

GC analysis of the diastereomers of the optically active alcohols used in synthesis of the enantiomers of the pheromone showed that each optical isomer of the alcohol contained 2% opposite enantiomer. Field tests were conducted in two open fields at the Beltsville Agriculture Research Center, Beltsville, Md.

Behavioral response assays were conducted in field tests. Male bagworm responses to the enantiomers and racemate of 1-methylbutyldecanoate were evaluated on cotton rolls or to a virgin female placed in wing sticky insect traps positioned 20 meters apart, 1.5 meters from the ground, and baited daily. The test was replicated 5 times on each of 5 days in mid-September, 1981, near Beltsville, Md. using a randomized complete-block design. The traps baited with 500 µg R enantiomer captured males at about the same rate as traps baited with 1000 μg racemate (Table 1). The small number of males attracted to the S enantiomer were most likely responding to the trace of R in the S isomer.

In tests for suppression or control, 5 to 6 ft arborvitae trees supported by soil in individual bushel baskets were placed along the perimeter of the field at 60 meter intervals. Individual bags of ten female pupae were secured at the apical tip with paper binder clips and secured to each tree with wire. Treated trees were decorated each with a spiral of plastic ribbon containing the racemic 1-methylbutyldecanoate. Ribbons were removed every four days and replaced with new ribbon.

The 1-methylbutyldecanoate in a crude extract of the females' pheromone-laden hairs was assayed by GC and field tested versus the same amount (5.5 μg/trap) of synthetic racemate. The number of males captured in traps baited with this extract was not different from those baited with the synthetic racemate. Thus, the superiority of the synthetic racemate over females in causing male capture, Table 1, is attributed to the comparatively small quantity of pheromone produced by the female.

The synthetic pheromone, is a racemic mixture, half of which is the same as the natural pheromone. The racemate is easy to synthesize and has the same attractant properties as the natural pheromone. Another great advantage of the synthetic racemate is the low production cost. Synthesizing the active component of the natural pheromone requires the optically pure alcohol which is considerably more expensive than its racemic form. As described above, isolating and purifying the active component of the natural pheromone is a time consuming and an expensive task.

Field tests were conducted as described above. Mating suppression as measured by the relatively few mated females was achieved with 1.2 grams of synthetic racemate per tree for 7 days, Table 2. A second test which showed a high degree of mating suppression on individual host plants was obtained with 1.2 grams of synthetic racemate per host plant for 17 days. Data from the second test indicates suppression occurred on control plants as well, Table 3. Complete control of mating occurred when each infested tree within the treatment area was similarly treated with 1.2 grams of synthetic racemate, Table 4.

TABLE 1

Male *Thyridopteryx ephemeraeformis* responses in field bioassay to racemate and R and S enantiomers of 1-methylbutyldecanoate identified from discharged hairs from the female.

| Treatment[1] | x male capture/trap/day[2] |
| --- | --- |
| 500 μg R | 27.3 a |
| 1000 μg racemate | 24.6 a |
| 100 μg racemate | 7.3 b |
| 50 μg R | 4.1 b |
| 1 virgin female | 3.0 c |
| 500 μg S | 2.1 cd[3] |
| 50 μg S | 0.2 e |

[1]Each enantiomer contains 2% of the opposite antipode.
[2]Means followed by the same letter are not significantly different from each other according to Ducan's New Multiple Range Test.
[3]Male responses to S enantiomer treatments were due to 2% R in the S enantiomer.

TABLE 2

Mating suppression of female bagworm moth with racemic 1-methylbutyldecanoate[1]

| Treatment[2] | Mated Females | Calling Female | Live Pupa | Total |
| --- | --- | --- | --- | --- |
| Racemic 1-methylbutyldecanoate | 0 | 23 | 17 | 40 |
| Control | 8 | 11 | 21 | 40 |

[1]September 18 through 24, 1981 (7days).
[2]Four of eight trees were decorated with a ribbon 0.25 in wide × 192 in long containing 25.0 mg (+,−) per in² or 1.200 g (+,−). Trees were spaced at 60 meter intervals at one field.

TABLE 3

Mating suppression of the female bagworm moth with racemic 1-methylbutyldecanoate[1]

| Treatment[1] | Mated Females | Calling; Unmated | Calling; Died | Dead Pupa | Live Pupa | Missing |
| --- | --- | --- | --- | --- | --- | --- |
| Racemic 1-methyl-butyl-decanoate | 6 | 22 | 57 | 10 | 0 | 5 |
| Control | 18 | 23 | 40 | 14 | 4 | 4 |

[1]September 8 through 24, 1982 (17 days).
[2]The test was conducted at 2 locations with 5 replicates each. In each replicate 10 unmated female pupae were attached to each host plant. One half of the plants were treated and decorated with a ribbon 0.25 in wide × 264 in long containing 17.5 mg (+,−) per in² or 1.155 g (+,−). The minimum distance between plants was 60 meters.

TABLE 4

Mating control of the female bagworm moth with racemic 1-methylbutyldecanoate[1]

| Treatment[1] | Mated Female | Calling; Unmated | Calling; Died | Dead Pupa | Live Pupa | Missing |
| --- | --- | --- | --- | --- | --- | --- |
| Racemic 1-methyl-butyl-decanoate | 0 | 7 | 41 | 49 | 3 | 0 |
| Control | 30 | 3 | 8 | 57 | 1 | 1 |

[1]September 27 through October 21, 1982 (25 days).
[2]Approximately 1 mile between treated and untreated. Each treatment included ten replicated host plants each with 10 pupae attached. Treated plants were 60 meters apart and similarly decorated with a ribbon 0.25 in wide × 192 in long containing 25 mg (+,−) per in² or 1.2 g (+,−).

We claim:

1. A method of attracting adult male bagworm moths comprising baiting a trap with an effective attractant amount of the synthetic racemate 1-methylbutyldecanoate.

2. The method of claim 1 wherein a trap is baited with an effective attractant amount of the R enantiomer of 1-methylbutyldecanoate.

3. A method of suppressing the mating of female bagworm moths in an area of trees and shrubs infested with bagworm moths and thereby protecting said trees and shrubs from damage comprising treating the trees and shrubs in the area with an effective mating suppressant amount of the synthetic racemate 1-methylbutyldecanoate.

4. The method of claim 3 wherein one-half of the trees and shrubs are treated with the synthetic racemate 1-methylbutyldecanoate.

5. The method of claim 3 wherein a plastic ribbon containing about 1.2 grams of the synthetic racemate 1-methylbutyldecanoate is applied as a spiral to each treated tree.

6. The method of claim 1 wherein the trap is baited with 1000 μg of the synthetic racemate 1-methylbutyldecanoate.

7. The method of claim 2 wherein the trap is baited with 500 μg of the R enantiomer of 1-methylbutyldecanoate.

* * * * *